(12) United States Patent
Ruiz-Vela et al.

(10) Patent No.: US 6,382,965 B1
(45) Date of Patent: May 7, 2002

(54) ORTHODONTIC DEBONDING TOOLS AND METHODS

(75) Inventors: Albert Ruiz-Vela, Alta Loma; Farrokh Farzin-Nia, Inglewood, both of CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 09/558,449

(22) Filed: Apr. 25, 2000

(51) Int. Cl.⁷ .................................................. A61C 3/00
(52) U.S. Cl. .................................................. 433/4; 433/9
(58) Field of Search ........................................ 433/4, 9

(56) References Cited

U.S. PATENT DOCUMENTS

| | | | |
|---|---|---|---|
| 4,435,160 A | 3/1984 | Randklev | 433/9 |
| 4,820,545 A | 4/1989 | Negrych | 427/2 |
| 4,902,224 A | 2/1990 | Collins et al. | 433/8 |
| 4,915,625 A | 4/1990 | Tsukuma et al. | 433/8 |
| 4,950,157 A | 8/1990 | Cleary | 433/4 |
| 5,011,403 A | 4/1991 | Sadoun et al. | 433/8 |
| 5,062,793 A | 11/1991 | Cleary et al. | 433/3 |
| 5,064,369 A | 11/1991 | Kawaguchi | 433/3 |
| 5,066,225 A | 11/1991 | Forbes Jones et al. | 433/8 |
| 5,161,969 A | 11/1992 | Pospisil et al. | 433/8 |
| 5,197,873 A | 3/1993 | Wong et al. | 433/9 |
| 5,261,814 A | 11/1993 | Farzin-Nia et al. | 433/8 |
| 5,288,230 A | 2/1994 | Nikutowski et al. | 433/20 |
| 5,366,372 A | 11/1994 | Hansen et al. | 433/4 |
| 5,380,196 A | 1/1995 | Kelly et al. | 433/8 |
| 5,439,379 A | 8/1995 | Hansen | 433/8 |
| 5,645,421 A | 7/1997 | Slootsky | 433/6 |

OTHER PUBLICATIONS

Ormco Corporation, inspire! Bracket Identification and Placement, Brochure, undated.
Ormco Corporation, For aesthetics, there is only one clearly superior choice . . . , Brochure, undated.
Samir E. Bishara et al., Evaluation of Debonding Characteristics of a New Collapsible Ceramic Bracket, Article, American Association of Orthodontists, 1997.
Unitek Corporation, Effects of Debonding Transcend Ceramic Orthodontic Brackets from Human Enamel: An In Vitro Examination, Article, 1988.
Ormco Corporation, Orthodontic Product Catalog, 1999 Catalog, pp. 12–13 and 32–33.
Samir E. Bishara et al., Comparisons of Different Debonding Techniques for Ceramic Brackets: An In Vitro Study, Part II. Findings and Clinical Implications, Am J Ortho, Sep. 1990.
Samir E. Bishara et al., Comparisons of the Effectiveness of Pliers with Narrow and Wide Blades in Debonding Ceramic Brackets, Am J Orthod, Mar. 1993.
Michael L. Swartz, Ceramic Brackets, Article, JCO 88 Feb 82–88.
Deva Devanathan, Design and Development of an Advanced Ceramic Bracket, Article, TP Orthodontics, Inc., 1997.
Ormco Corporation, It's time to take a closer look at aesthetics . . . , Brochure, undated.
Samir E. Bishara et al., Comparisons of Different Debonding Techniques for Ceramic Brackets: An In Vitro Study, Part I. Background and Methods, Article, Am J. Orthod, Aug. 1990.

*Primary Examiner*—Nicholas D. Lucchesi
(74) *Attorney, Agent, or Firm*—Wood, Herron & Evans, L.L.P.

(57) ABSTRACT

Debonding tools and methods especially useful for removing ceramic brackets adhesively bonded to the teeth of a patient. In general, the tool and methods involve applying a tensile force to one side of the bracket while avoiding point loading which may cause the bracket to break. The tensile force may be applied by grasping the bracket with a tool having two jaws and pivoting the tool and the bracket about an axis generally lying in an occlusal-gingival plane of the tooth. At least the portions of the jaws that engage the bracket are formed from a material having a substantially reduced hardness relative to the brittle material of the bracket. Other embodiments of the tool engage a recess, such as one disposed beneath a tie wing, and pry the bracket away from the tooth.

14 Claims, 7 Drawing Sheets

ORTHODONTIC DEBONDING TOOLS AND METHODS

FIELD OF THE INVENTION

The present invention generally relates to tools and methods for removing or debonding orthodontic brackets which have been affixed to the teeth of a patient with an adhesive bonding material. More particularly, the tools and methods relate to debonding procedures intended to be carried out without breaking or fracturing brackets formed from hard, brittle materials, such as ceramic materials.

BACKGROUND OF THE INVENTION

One of the major challenges associated with the use of ceramic brackets for orthodontic treatment is the removal of the brackets from the teeth of the patient. Metal brackets are generally removed by pinching the brackets in a generally mesial-distal or diagonal direction using a pair of pliers, such as so-called Weingart pliers. The pliers apply compressive forces and pinch the brackets generally in a mesial-distal direction, typically by placing the jaws of the pliers diagonally across the bracket and engaging tie wings at opposite corners of the bracket, for example, at the gingival/mesial and occlusal/distal corners. Pinching the metal bracket in this manner results in deformation of the ductile bracket body as well as the bonding pad used to attach the body to the tooth. This deformation causes a separation or fracture at the interface between the adhesive and the bonding pad or base and essentially peels the bracket away from the tooth as the adhesive material fractures or debonds.

Brittle orthodontic bracket materials, such as ceramic materials, are much more problematic during the bracket removal or debonding process. These bracket materials are extremely hard and non-ductile relative to the materials, such as stainless steel, typically used for metal brackets. Ceramic materials also have a low fracture toughness relative to steels and other metals, meaning that ceramic material is much more prone to fracture under an applied force rather than deforming under the applied force. An attempt to pinch the wings of a ceramic bracket in the manner described above for metal brackets generally results in fracture of the tie wings or other portions of the bracket due to point loading of the bracket material by the pliers at the contact points. For this reason and other reasons, such as heightened sensitivity to surface imperfections, various alternative debonding tools and methods have been proposed and used, however, none have been fully satisfactory.

As an example, plier-type tools having metal jaws with sharp, opposed edges have been used in the past with the sharp edges intended to be directed into the adhesive interface between the bracket base and the tooth of the patient. The jaws are then squeezed together in an effort to separate the base from the tooth by the application of forces directly to the adhesive interface. The problem with this tool and method is that it is often very difficult to accurately align and maintain the sharp edges of the jaws at the adhesive interface as the handles of the plier-type tool are squeezed to apply the requisite debonding forces. Another tool and method has involved gripping the bracket on its mesial and distal sides and using a torsional force to rotate the bracket about an axis perpendicular to the base of the bracket and shear the adhesive interface. The torsional force applied by this method can be very uncomfortable for the patient and often requires excessive force that could also be harmful to the tooth structure. Another past method and tool involves grasping occlusal and gingival sides of the bracket and pulling the bracket directly away from the tooth along an axis perpendicular to the bracket base. This method also requires an excessive amount of force making it difficult to separate the bracket from the tooth, and can result in damaging the tooth surface. Finally, a more recent method for debonding ceramic brackets involves compressing or pinching together mesial and distal sides of the bracket to fracture the bracket along a midline in a direction parallel to the tooth surface and perpendicular to the archwire slot.

To overcome various problems with debonding tools and methods of the past, and especially tools and methods for debonding hard, brittle brackets such as ceramic brackets, new tools and methods are needed for effectively debonding the bracket in one piece without breakage or fracture of the bracket and with minimal force, discomfort, and potential for harmful effects on the patient.

SUMMARY OF THE INVENTION

In one aspect, the present invention provides an orthodontic debonding tool for compressively gripping a nonmetallic, hard and brittle bracket, such as a ceramic bracket, which is bonded with an adhesive to a tooth of a patient. The tool includes a first jaw having an outer end with a bracket-engagement portion and a second jaw also having a outer end with a bracket-engagement portion. The second jaw is coupled to the first jaw to allow movement of at least one of the first and second jaws between an engaged position in which the bracket-bracket-engagement portions grip opposite sides of the bracket, preferably gingival and occlusal sides thereof, and a disengaged position for releasing the grip on the bracket. At least the bracket-engagement portions of the first and second jaws are formed from a material having a hardness sufficiently less than the hardness of the ceramic bracket so as to substantially reduce the probability of the bracket breaking or fracturing when the bracket-engagement portions of the jaws grip the bracket on opposite sides with a compressive force.

During debonding, a pivoting motion is applied to the first and second jaws about an axis generally lying in a plane parallel to the plane of the bracket base surface, i.e., the surface that abuts the tooth. In this manner, a tensile force is applied to one side of the bracket in a direction away from the tooth and the adhesive is fractured without breaking or fracturing the ceramic bracket. Alternatively, a compressive force directed toward the tooth, a smaller tensile force directed away from the tooth, or essentially no force may be exerted along the opposite side of the bracket to facilitate the pivoting motion. The "sides" of the bracket under the applied force(s) may be occlusal, gingival, mesial or distal sides, or a combination thereof such as a bracket corner.

The tool preferably includes first and second handles respectively connected to the first and second jaws with the handles adapted to be gripped by user and moved with respect to each other to apply the compressive force to the bracket. The first and second jaws may be integrally formed with the respective first and second handles, for example, by molding from a nonmetallic material such as plastic or a plastic composite. One advantage to such a construction is that the tool may be economically fabricated or formed as a disposable item and discarded after use on the brackets of a particular patient. In the preferred embodiment, the jaws and handles are formed from a glass-filled polycarbonate material, however, many other materials which are substantially softer than the conventional ceramic bracket materials may be used as well, including ductile metals, such as titanium, aluminum, brass, zinc or various metal alloys.

Other materials useful for at least the engagement portions of the tool include, but are not limited to, polysulfones. Thermoplastic materials, thermoset materials, rubbers, other polymeric materials or even wood may be used for at least the bracket-engagement portions as well.

At least the bracket-engagement portions of the first and second jaws should have a modulus of elasticity less than about $15 \times 10^6$ psi. More preferably, the modulus of elasticity for those portions of the tool configured to contact the bracket should be less than about $5 \times 10^6$ psi. In terms of hardness, at least the bracket-engagement portions of the first and second jaws should have a Knoop microhardness of less than about 500 and, more preferably, less than about 300. This is substantially less than the Knoop microhardness of conventional ceramic bracket materials which typically have a Knoop microhardness of at least about 1,000–1,500 and more typically about 2,000. The orthodontic brackets suitable for use with the present invention have a modulus of elasticity higher than about $20 \times 10^6$ psi. The fracture toughness of the bracket material is preferably less than about 20 MPa$\sqrt{m}$ and, more preferably, less than about 10 MPa$\sqrt{m}$.

Conventional metal brackets, on the other hand, have a fracture toughness of at least about 50 MPa$\sqrt{m}$. The significant difference between the modulus of elasticity and/or the hardness of the bracket-engagement portions and the bracket help ensure that point loading on the bracket does not occur as the jaws of the tool apply compressive force to grip the bracket and thereafter pivot to apply unequal debonding forces in the tensile direction. Instead, the bracket-engagement portions will slightly yield against the harder, more brittle bracket material and spread the applied forces across a wider area of the bracket. As the tensile force is applied, the adhesive interface will fracture or debond before the forces reach a level that could cause the bracket to fracture.

A force limiting feature may also be incorporated into the tool. For example, the bracket-engagement portion or portions may be designed to break or deform at a specified level of force which is lower than the force necessary to fracture the bracket or damage the tooth enamel. Optionally, the handles or other portions of the tool may be designed to contact each other to prevent further compressive movement of the jaws which could fracture the bracket or, during a pivoting motion, damage the tooth enamel.

In a more specific embodiment, the bracket-engagement portions of the first and second jaws include respective first and second nibs projecting toward each other in the engaged position from respective side walls of the engagement portions which extend transverse to the nibs. The nibs are configured to respectively engage recesses on opposite sides of the bracket, such as the recesses that are typically disposed between opposite tie wings of the bracket and the bracket base. In this embodiment, the side walls of the engagement portions preferably contact and apply a compressive, bracket-gripping force to the opposite tie wings of the bracket while the nibs are engaged in the recesses below the tie wings. The tool may then be pivoted in the manner described above to apply a tensile force to at least one side of the bracket in a direction away from the tooth and fracture the adhesive bond between the bracket base and the tooth without fracturing the bracket.

In another embodiment of the invention, a debonding tool comprises an elongate member having a longitudinal axis, a first or outer end adapted to be gripped by a user, and a second or inner end. A bracket-engagement member is disposed on the second end and extends generally transverse to the longitudinal axis for engaging a recess in a side wall of the bracket. A tooth-engagement member is located on the second end, preferably at the extremity of the second end outside of the bracket-engagement member, and lies generally along the longitudinal axis. The tooth-engagement member acts as a fulcrum when the bracket-engagement member is engaged with the recess and a prying motion is applied by pivoting the elongate member with respect to the bracket about an axis lying in a plane generally parallel to the plane of the bracket base surface, i.e., the surface facing the tooth. This pivoting action applies a tensile force along the recessed side wall of the bracket in a direction away from the tooth to fracture the adhesive between the bracket base and the tooth without fracturing the bracket. The bracket-engagement member and the tooth-engagement member preferably comprise respective projections extending from the second or inner end of the elongate member in directions which are generally perpendicular to each other. This tool may also be comprised of metallic or nonmetallic materials and may be formed from harder materials than the first embodiment since a compressive force is not being applied during its use, although at least the bracket-engagement member should be sufficiently softer than the bracket to avoid fracturing the bracket during debonding. Like the first embodiment, it is preferred that this tool be a disposable or single-use product, however, since it may be formed from harder materials, it may be even more appropriate as a reusable tool.

Generally, a method of debonding a nonmetallic bracket in accordance with the invention includes engaging at least a first side of the bracket, pivoting the bracket about an axis lying in a plane which is generally parallel to the plane of the bracket base surface to apply a tensile force to the first side of the bracket in a direction away from the tooth, and fracturing the adhesive bond between the bracket and the tooth under the tensile force applied to the first side to remove the bracket in a single piece. In one embodiment, the method involves engaging first and second opposite sides of the bracket with the tool and applying a compressive gripping force to the bracket prior to pivoting the tool.

In another general embodiment, a method of debonding a bracket having at least one tie wing on each of two opposite sides of the bracket base, and at least one recess disposed between the base and each tie wing, includes engaging the bracket with a portion of a tool positioned in at least one of the recesses, moving the tool portion about an axis lying in a plane generally parallel to a plane of the bracket base surface to apply a tensile force to the corresponding side of the base in a direction away from the tooth, and fracturing the adhesive between the bracket base and the tooth without fracturing or breaking the bracket. In the preferred embodiment of the methods of this invention, the bracket is formed from a hard, brittle, and fracture-prone material as compared to relatively ductile brackets formed from metal with a general example being a ceramic material.

Another debonding method in accordance with the invention includes engaging at least one tool engagement portion of a ceramic bracket with a debonding tool, moving the tool to apply unequal forces to opposite sides of the ceramic bracket with a greater tensile force being applied in a direction away from the tooth, and fracturing the adhesive bond between the base of the bracket and the tooth beginning at the side under the greater force and without breaking the ceramic bracket. The force on the opposite side, or pivot axis side, of the bracket may be essentially zero, or be a compressive force, or be a smaller tensile force directed away from the tooth.

Various additional features, objectives and advantages of the tools and methods summarized above will become more readily apparent to those of ordinary skill in the art, upon review of the following detailed description of the preferred embodiments taken in conjunction with the accompanying drawings.

DETAILED DESCRIPTION OF THE PREFERRED EMBODIMENTS

Figure 1:
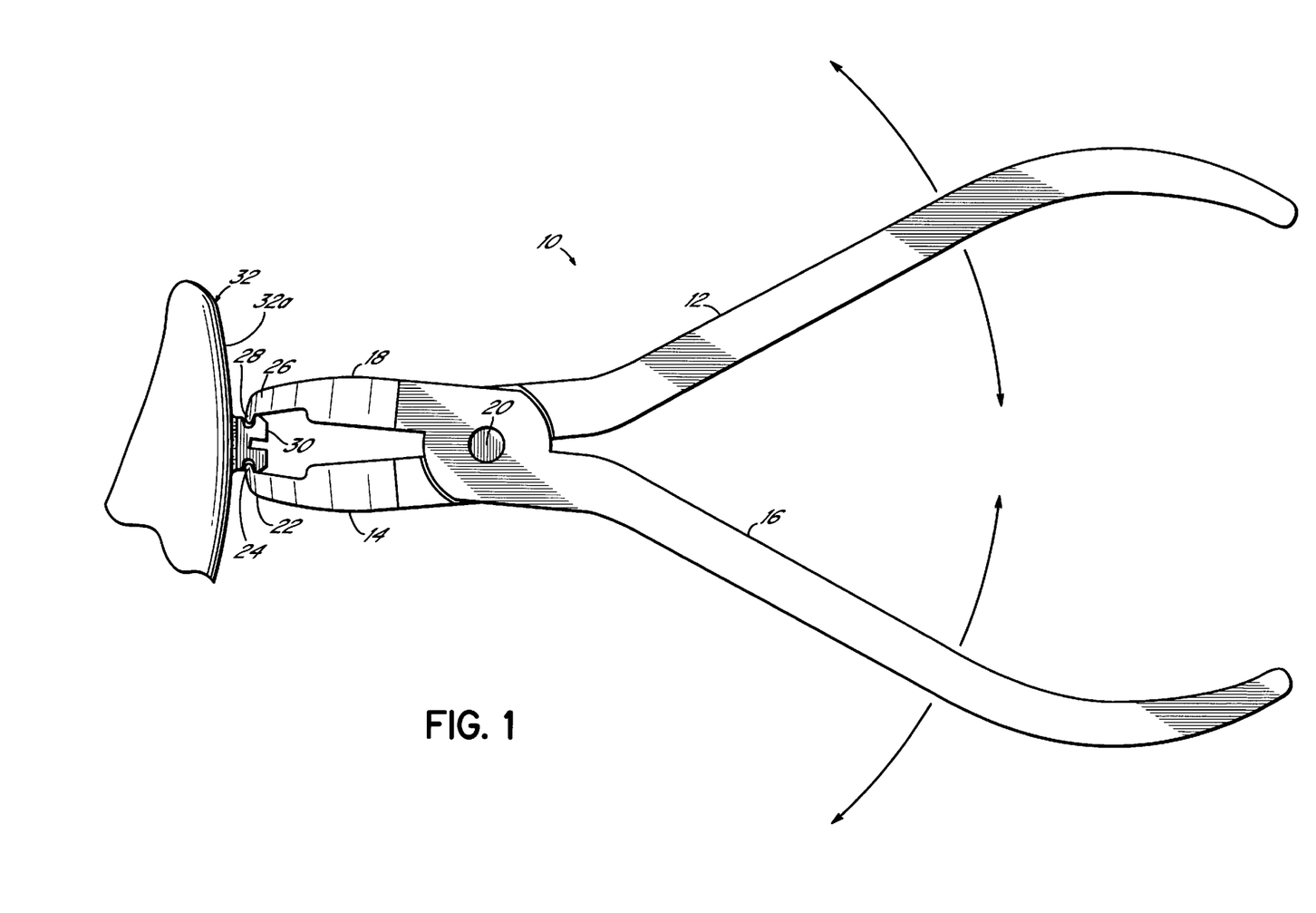
FIG. 1 is a side elevational view showing a preferred tool of the present invention gripping an orthodontic bracket which is adhesively bonded to a tooth.

FIG. 1 generally illustrates a tool 10 constructed in accordance with one preferred embodiment of the invention. Tool 10 takes the general form of a pair of pliers having a first handle 12 preferably formed integrally with a first jaw 14 and a second handle 16 also preferably formed integrally with a second jaw 18. Handle and jaw 12, 14 are pivotally coupled to handle and jaw 16, 18 by a pivot pin 20. First jaw 14 includes a first bracket-engagement portion 22 having a first nib 24 and second jaw 18 includes a second bracket-engagement portion 26 having a second nib 28. Nibs 24, 28 project toward one another, as shown in FIG. 1, when engagement portions 22, 26 are in an engaged position gripping an orthodontic bracket 30 which has been adhesively affixed to an outer surface 32a of a tooth 32. The present invention is applicable to brackets which have been directly chemically bonded to the teeth with one or more adhesive agents or brackets which include an adhesive component and/or mechanical bonding base component, such as balls, projections, etc., between the bracket and the tooth. During debonding according to this invention, all or some of the bonding base components may be compromised in some manner, such as by being left on tooth surface 32a, while bracket 30 debonds in one piece. In general, the bond strength should be less than the strength of tool 10 so that tool 10 does not fail prior to the bond. Typically, bond strengths will range from 10 Kg–20 Kg. If the bond strength is much higher, such as at 25 Kg–35 Kg and above, tooth damage could occur during debonding. As one feature, the present invention avoids this potential damage by providing one or more force limiting features for tool 10 as discussed below. Handles 12, 16 may be moved away from each other to disengage bracket 30 and moved toward one another, as shown in FIG. 1, to engage or grip bracket 30.

Figure 2:
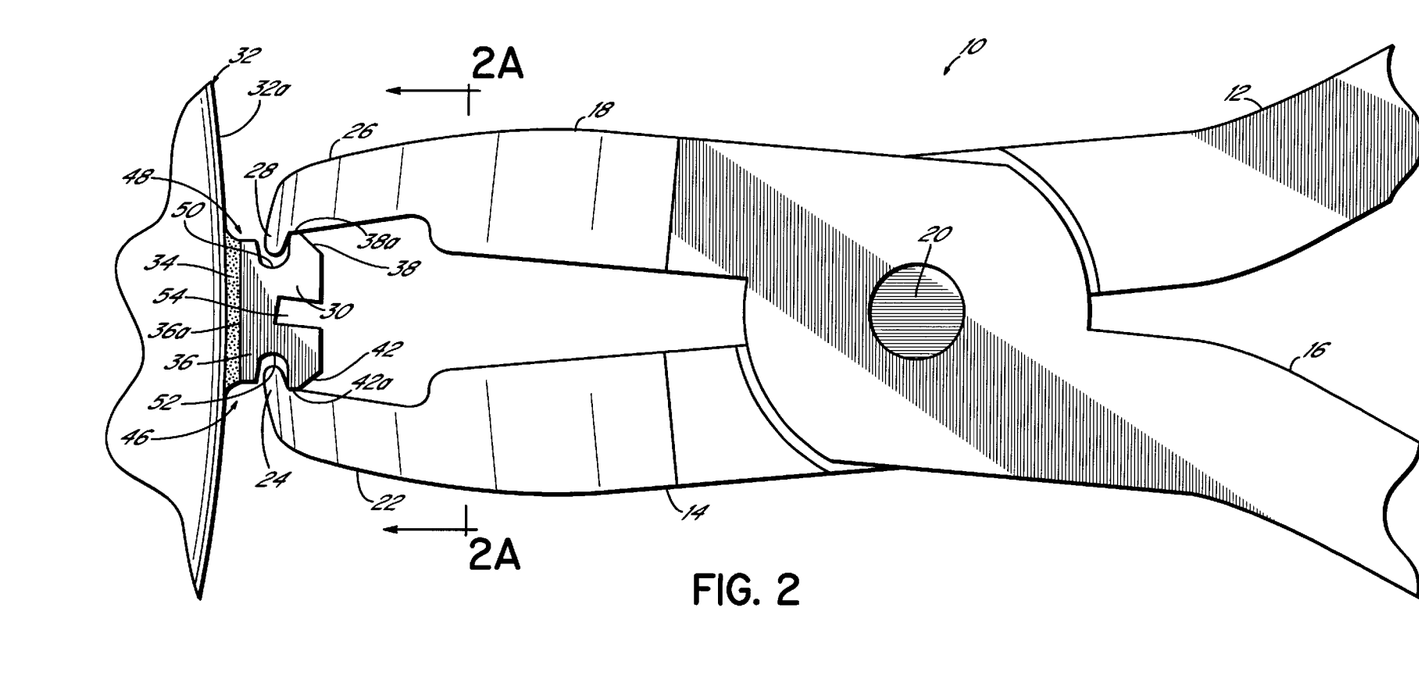
FIG. 2 is a fragmented, enlarged view showing the engagement of the jaws with the orthodontic bracket.
Figure 2A:
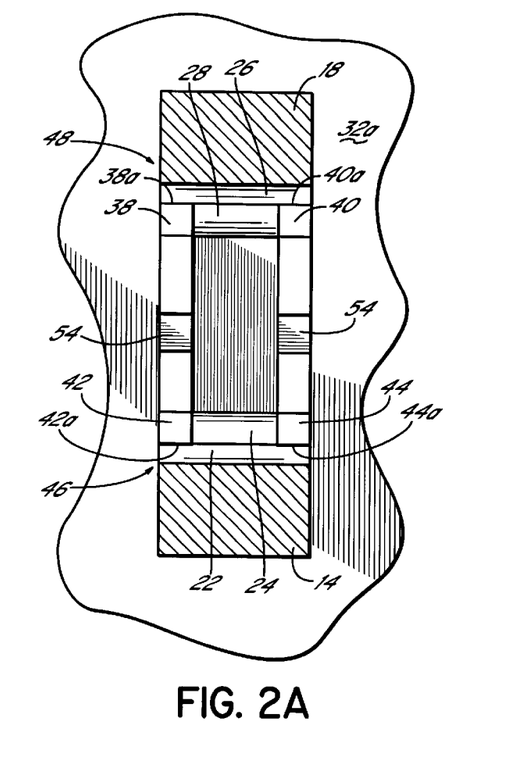
FIG. 2A is a cross sectional view taken along line 2A—2A of FIG. 2.

Turning to FIGS. 2 and 2A, bracket 30 is bonded to tooth surface 32a by at least one adhesive layer 34 which is schematically illustrated as a single layer but may take many different forms as generally appreciated by those of skill in the art. Often, this adhesive layer and/or bracket base or bonding pad 34 includes various elements to facilitate mechanically bonding bracket 30 and tooth surface 32a. Bracket 30 can further include a plurality of tie wings 38, 40 and 42, 44 on opposite gingival and occlusal sides 46, 48. In this conventional configuration, a recess 50 is provided between base 36 and tie wings 38, 40 and an opposite recess is provided between base 36 and tie wings 42, 44. An archwire slot 54 runs in a mesial-distal direction between the respective pairs of tie wings 38, 40 and 42, 44.

Figure 1A:
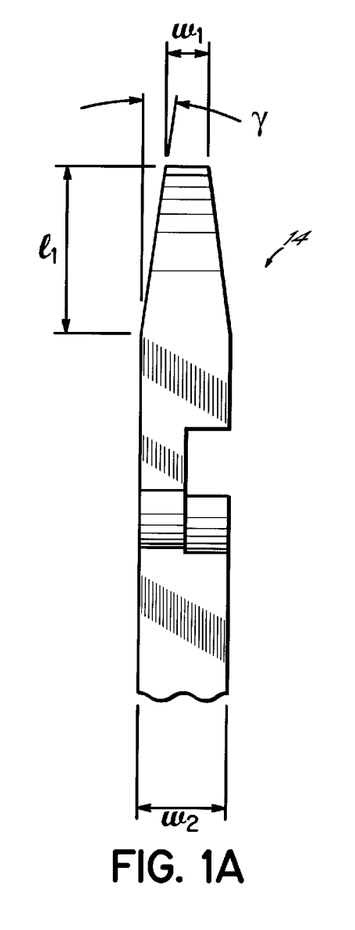
FIG. 1A is a fragmented view of one of the tool jaws shown in front elevation.
Figure 1B:
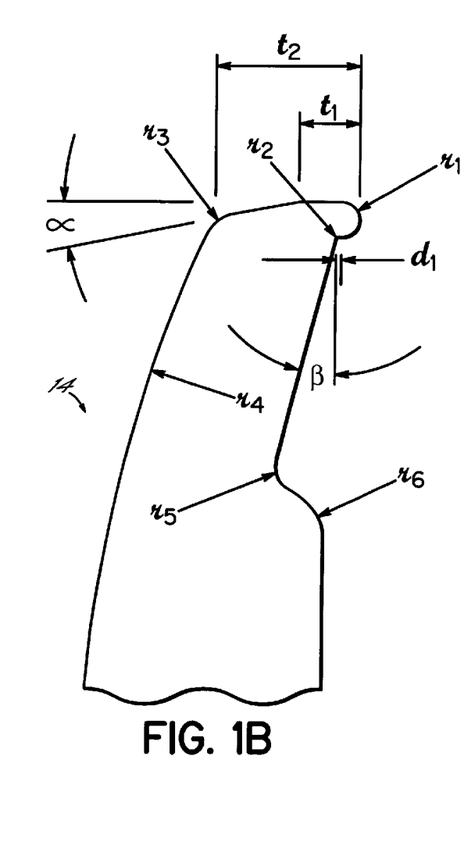
FIG. 1B is a fragmented view showing the jaw of FIG. 1A in side elevation.

Tool 10 is preferably formed of plastic material as a disposable, single-use article which may be used for debonding the brackets of a single patient and then discarded when the debonding process is complete. This may be accomplished in an economical manner by injection molding or otherwise molding the various component parts of tool 10. For the additional comfort and safety of the patient, and/or to further ensure that bracket 30 does not fracture due to compression by jaws 14, 18, nibs 24, 28 may be formed as breakaway or deformable elements which act as a limit on the applied compression by deforming or breaking at a predetermined load limit. Also, under such an increased load which may be uncomfortable or unsafe for the patient, at least one of the nibs, such as nib 28 shown in FIG. 3, will break away or deform before the force imposed by the pivoting action of tool 10 becomes too great. As another manner of limiting the applied forces, handles 12, 16 can have ends 12a, 16a which contact each other to stop further compressive movement of jaws 14, 18 and therefore stop the compressive force at a predetermined limit which is below the force necessary to fracture the bracket. FIGS. 1A and 1B illustrate the dimensions of jaw 14 in the preferred embodiment. In particular, the preferred dimensions are as follows:

| Symbols | Corresponding Dimensions |
| --- | --- |
| $w_1$ | 0.140 inch |
| $w_2$ | 0.302 inch |
| $l_1$ | 1.02 inch |
| Y | 8° (each side) |
| α | 10° |
| β | 15° |
| $t_1$ | 0.050 inch |
| $t_2$ | 0.125 inch |
| $d_1$ | 0.005 inch |
| $r_1$ | 0.015 inch |
| $r_2$ | 0.003 inch |
| $r_3$ | 0.025 inch |
| $r_4$ | 1.250 inch |
| $r_5$ | 0.025 inch |
| $r_6$ | 0.050 inch |

These dimensions are only illustrative of the preferred embodiment construction with 30% glass-filled polycarbonate. Those of ordinary skill in the art will readily appreciate that the dimensions, configurations, and materials of construction may be modified in various manners while still achieving one or more of the functions stated herein for tool 10.

When tool 10 is in the engaged or gripping position shown in FIGS. 2 and 2A, nib 24 is retained within recess 52 and nib 28 is retained in recess 50. Bracket-engagement portions 22, 26 also make full line contact with tie wings 38, 40, 42, 44 along edges 38a, 40a, 42a, 44a. This full contact allows better gripping and avoids point loading of bracket 30 which could result in breaking or fracturing the bracket as compression is applied by jaws 14, 18. To further avoid breaking or fracturing bracket 30, and especially breaking one or more of the tie wings 38, 40, 42, 44, at least bracket-engagement portions 22, 26, including nibs 24, 28, are formed from a relatively soft material as compared to bracket 30. In the preferred embodiment, the entire tool 10, except for pivot pin 20 which may be metallic, is formed from a 30% glass-filled polycarbonate material which has a modulus of elasticity of about $1 \times 10^6$ psi. However, other metallic or nonmetallic materials may be used to partially or entirely form or fabricate tool 10 as long as bracket-engagement portions 22, 26 are formed from a significantly more ductile or soft material than bracket 30. As general guidelines, the modulus of elasticity of the material forming at least bracket-engagement portions 22, 26 should be less than about $15 \times 10^6$ psi and preferably less than about $5 \times 10^6$ psi. The Knoop microhardness of at least portions 22, 26 which engage and contact bracket 30 should be less than about 500 and, more preferably, less than about 300. By comparison, a typical ceramic bracket will have a Knoop microhardness of at least about 1,000 and, more typically, about 2,000 and have a modulus of elasticity in excess of $20 \times 10^6$ psi.

Figure 3:
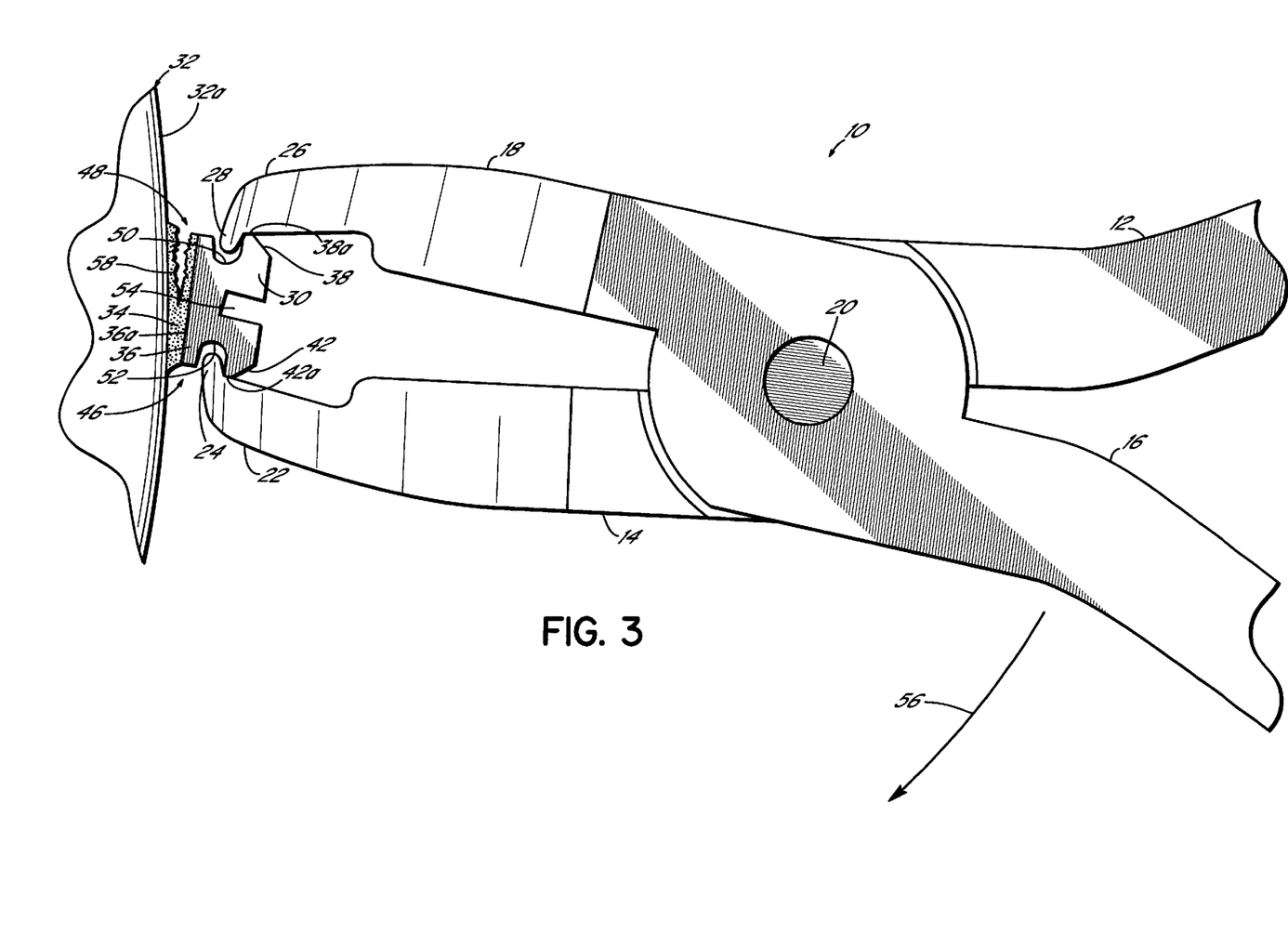
FIG. 3 is a side elevational view similar to FIG. 2, but showing the tool rotated to break the adhesive bond between the bracket and the tooth.

FIG. 3 illustrates rotation of tool 10 in a direction indicated by arrow 56 while grip pressure or compression is maintained on bracket 30 with engagement portions 22, 26 and opposed nibs 24, 28. A compressive grip is maintained on bracket 30 with nibs 24, 28 to permit a pivoting motion to be applied to bracket 30 and apply the required tensile force without having engagement portions 22, 26 and opposed nibs 24, 28 slip off bracket 30 while attempting to pivot bracket 30. This rotation in the direction of arrow 56 takes place about an axis lying in a plane generally parallel to the plane of base surface 36a, i.e., generally in the plane of tooth surface 32a as shown in FIG. 2A. In this manner, a tensile force is applied along occlusal side 48 of bracket 30 in a direction away from tooth surface 32a. At the same time, compressive forces are applied to bracket 30 along the opposite gingival side 46 in a direction toward tooth surface 32a. In other words, unequal forces are applied in the tensile direction, i.e., a direction toward or away from tooth surface 32a and the greater tensile force applied in a direction away from tooth surface 32a causes adhesive layer 34 to fracture or debond beginning along the gingival edge of adhesive layer 34. Once a fracture 58 or debonding begins in this manner, the fracture essentially propagates across this adhesive interface to the opposite side of bracket 30, and bracket 30 debonds from tooth surface 32a in a single, unbroken piece.

FIG. 3 illustrates a portion of adhesive layer 34 remaining on tooth surface 32a and another portion remaining on bracket base 36. Depending on the application, more or less of the adhesive layer 34 may be stripped from tooth surface 32a during this debonding process. The term fracture is used herein in a manner referring to each of these potential situations, i.e., some adhesive remaining on the tooth or no adhesive remaining on the tooth. A similar method may be performed in accordance with the invention by gripping mesial and distal sides of bracket 30 with bracket-engagement portions 22, 26 and thereafter pivoting tool 10 about an axis generally lying in the plane of base surface 36a. However, this is not preferred with brackets of the type illustrated due to the potential for losing the grip on the mesial and distal sides. It will be appreciated, however, that such a method is possible in accordance with the inventive concepts, especially through the development of other gripping or prying tools adapted to the bracket.

Figure 4:
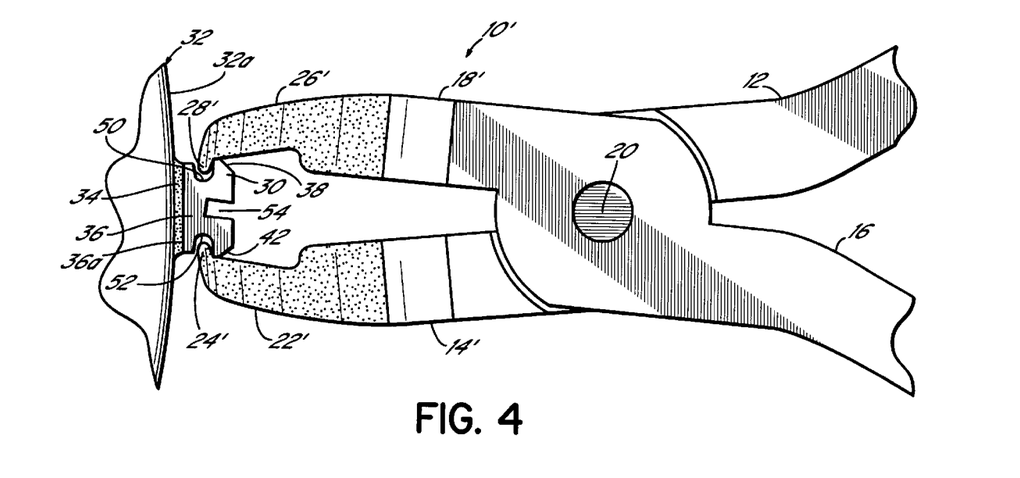
FIG. 4 is a side elevational view similar to FIG. 2, but showing an alternative embodiment of the tool.

FIG. 4 illustrates an alternative tool 10'. In this embodiment, like reference numerals indicate like elements with respect to the embodiment shown in FIGS. 1–3 and reference numerals with prime marks (') indicate modified elements. This embodiment is identical to the embodiment shown in FIGS. 1–3 except that jaws 14', 18' have been modified to include engagement portions 22', 26' formed from a different and softer material than the remaining portions of jaws 14', 18' and handles 12, 16. Portions 22', 26' may, for example, be formed of a nonmetallic material, while the remainder of tool 10' is formed from a standard metal for orthodontic tools, such as 316 stainless steel. In addition, portions 22', 26' may be removable portions which are used for one patient and then removed, discarded, and replaced for the next patient. Portions 22', 26' may be formed as relatively soft covers or boots for jaws 14', 18' or may be solid, relatively soft inserts suitably affixed to jaws 14', 18'.

Figure 5:
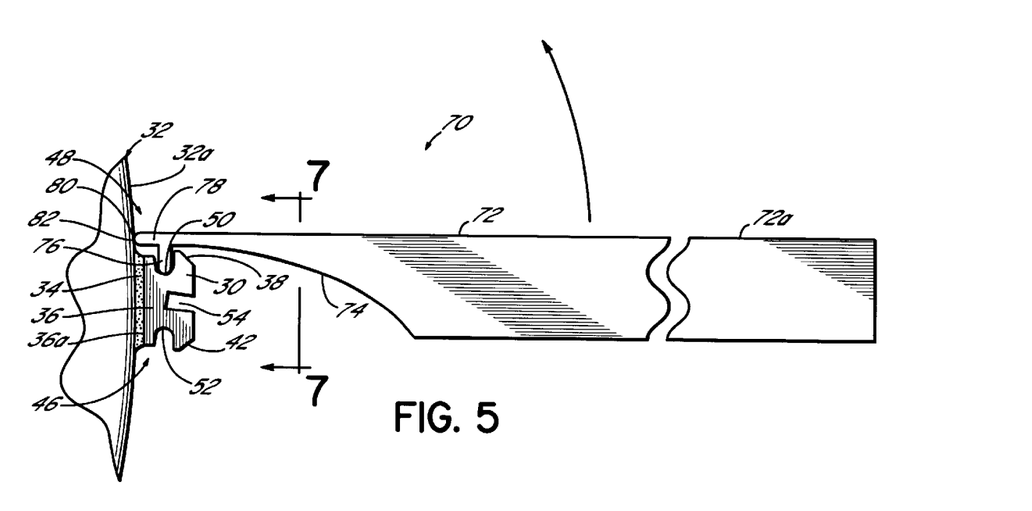
FIG. 5 is a side elevational view showing another alternative tool constructed in accordance with the invention and engaging an orthodontic bracket which is adhesively bonded to a tooth.
Figure 6:
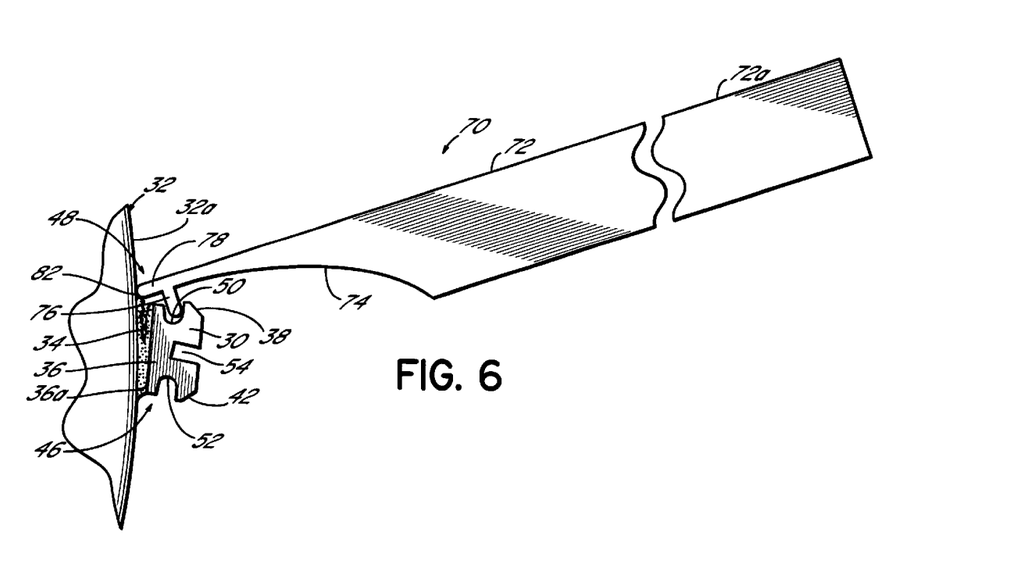
FIG. 6 is a side elevational view of the tool shown in FIG. 5 shown rotated to break the adhesive bond between the bracket and the tooth.
Figure 7:
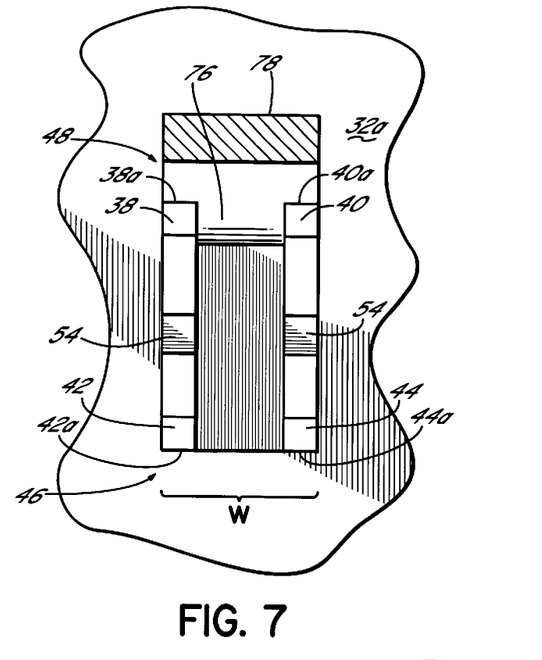
FIG. 7 is a cross sectional view taken along line 7–7 of FIG. 5.

FIGS. 5–7 illustrate an alternative tool 70 constructed in accordance with the inventive concepts. In this embodiment, like reference numerals indicate like elements with respect to the bracket and tooth shown in FIGS. 1–4. Tool 70 comprises an elongate member 72 having an outer end 72a adapted to be gripped by the user and having a tapered section 74 at an opposite end. The end of tapered section 74 includes a bracket-engagement member 76 and a tooth-engagement member 78. Tooth-engagement member 78 extends generally along a longitudinal axis 80 of elongate member 72 and bracket-engagement member 76 extends generally perpendicular to both tooth-engagement member 78 and axis 80. Tooth-engagement member 76 makes contact with tooth surface 32a at a point 82 directly adjacent to an edge of adhesive layer 34. Bracket-engagement member 76 is inserted within recess 50. Preferably, the width "w" of the bracket-engagement member 76, as shown in FIG. 7, is approximately as wide as the bracket measured in a mesial-distal direction. When elongate member 72 is gripped at end 72a and rotated in the direction of arrow 73 (FIG. 5) to the position shown in FIG. 6, the outer extremity 78a of tooth-engagement member 78 will act as a fulcrum and the tooth-engaging member will rotate about point 82 to cause the bracket-engaging member 76 to apply a tensile force to side 48 of the bracket engaged with member 76 in a direction away from tooth surface 32a. This tensile force is similar to the tensile force applied by tool 10 and 10', as shown in FIG. 3. Like the previous embodiments, a tensile force is applied to substantially only one side of bracket 30 and, preferably, to either the respective gingival or occlusal sides 46, 48 to cause a fracture 34 or to otherwise cause debonding starting at the side undergoing the greatest tensile force in a direction away from tooth surface 32a. In the embodiment of FIGS. 5–7, however, only one side of bracket 30 is engaged by a tool which, in this case, takes the form of tool 70 acting in a prying manner similar to the action of a crowbar.

It will be appreciated that many other forms of tools, including other specific configurations, constructions and materials, may be used to achieve similar results. While the embodiment shown in FIGS. 5–7 may also be formed of many types of materials, it is not as important in this embodiment that the engagement members be formed of a material significantly softer than the material of bracket 30. This is because there is no compressive force being applied to the bracket as in the previous embodiments. In fact, to achieve the prying effect the engagement members 76, 78, as well as remaining portions of tool 70, should be formed from more rigid materials such as aluminum capable of withstanding the bending stresses applied during rotation of tool 70 as the bracket is debonded from tooth 32.

Figure 8:
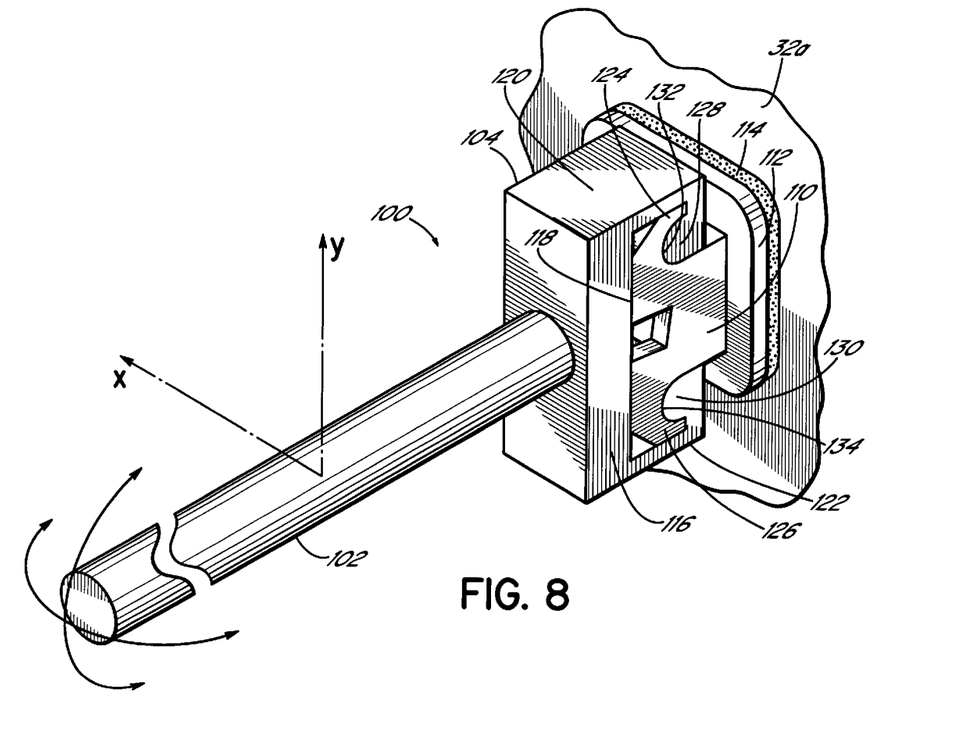
FIG. 8 is a perspective view of an alternative tool which may be pivoted in a mesial/distal direction or in an occlusal/gingival direction to remove a bracket in one piece.

FIG. 8 illustrates another alternative tool 100 constructed and used in accordance with the invention. Tool 100 includes a handle 102 rigidly connected to a generally hollow body 104 configured to engage a bracket 110 which, again, preferably comprises a relatively hard and brittle bracket formed from a ceramic material. Bracket 110 includes a base 112 and at least one layer of adhesive 114 for bonding bracket 110 to a tooth surface 32a. Hollow body 104 more specifically comprises a wall 116 generally extending in the occlusal-gingival direction from handle 102 and abutting an outer or labial surface 118 of bracket 110. A pair of side walls 120, 122 extend generally in the labial-lingual direction and abut tie wings 124, 126. A pair of projecting elements 128, 130 extend beneath tie wings 124, 126 into recesses 132, 134. It will be appreciated that hollow body 104 may be slid into the position shown from either the mesial or distal side of bracket 110 generally along the x-axis.

In the position shown in FIG. 8, tool 100 may be pivoted about an axis lying generally in the plane of base 112 or, in other words, in the x-y plane or the plane of tooth surface 32a. For example, the pivoting motion may be generally about the x-axis in an occlusal-gingival direction, or about the y-axis in a mesial-distal direction. In each case, the method will be performed with the same type of pivoting motion previously described for starting a fracture or debonding of adhesive layer 114 at one side of base 112 while pivoting bracket 110 about an axis generally defined along an opposite side thereof. Tool 100 may be formed from metal or plastic or plastic composites, for example, with the hardness of the material not being as critical a factor as with a tool that will grip bracket 110. In accordance with one aspect of the invention, however, tool 100 will be formed as a disposable, single-use tool as with the other embodiments of the invention.

While the present invention has been illustrated by a description of the preferred embodiments and while these embodiments have been described in some detail, it is not the intention of the Applicants to restrict or in any way limit the scope of the appended claims to such detail. Additional advantages and modifications will readily appear to those skilled in the art. Various features of the embodiments described herein may be combined in different manners depending on the desired characteristics. This has been a description of the present invention, along with the preferred methods of practicing the present invention as currently known. However, the invention itself should only be defined by the appended claims, wherein we claim:

What is claimed is:

1. A method of debonding a nonmetallic bracket having a base surface which is bonded to a tooth of a patient with an adhesive, the method comprising:

engaging at least a first side of the nonmetallic bracket, pivoting the nonmetallic bracket about an axis lying in a plane generally parallel to a plane defined by the base surface to apply a tensile force to the first side of the nonmetallic bracket in a direction away from the tooth, the tensile force applied to the first side being substantially greater than any tensile force directed away from the tooth which may be applied to the side of the bracket located opposite to the first side, and fracturing the adhesive between the nonmetallic bracket and the tooth under the tensile force applied to the first side of the nonmetallic bracket to remove the nonmetallic bracket from the tooth in a single piece.

2. The method of claim 1, wherein the step of engaging at least the first side further comprises:

engaging said first side and an opposite second side with a tool, and applying compressive forces to the first and second sides with the tool to grip the bracket prior to pivoting the tool.

3. The method of claim 2, wherein the step of engaging said first side and said opposite second side with the tool further comprises gripping the first and second sides of the bracket with at least a portion of the tool formed from a material of sufficiently reduced hardness relative to the bracket to avoid fracturing the bracket during the pivoting step.

4. The method of claim 3, wherein the material is a nonmetallic material.

5. The method of claim 3, wherein the material is a ductile metallic material.

6. The method of claim 2, wherein the step of engaging said first side and said opposite second side with the tool further comprises engaging recesses on the first and second sides of the bracket with respective projections extending from said tool.

7. A method of debonding a bracket affixed to a tooth of a patient with an adhesive located between a base surface of the bracket and the tooth, the bracket further including at least one tie wing on each of two opposite sides of the base, and at least one recess disposed between the base and each tie wing, the method comprising:

engaging the bracket with a portion of a tool positioned in at least one of the recesses, pivoting the tool portion about an axis lying in a plane generally parallel to a plane of the base surface to apply a tensile force to the first side of the base in a direction away from the tooth, the tensile force applied to the first side being substantially greater than any tensile force directed away from the tooth which may be applied to the side of the tooth located opposite to the first side, and fracturing the adhesive between the bracket base and the tooth without fracturing the bracket.

8. The method of claim 7, wherein the engaging step further comprises:

engaging each recess with different portions of the tool, and applying a compressive force with the tool to grip the bracket prior to pivoting the tool.

9. The method of claim 7, wherein the engaging step further comprises:

engaging each of the recesses with different portions of the tool, and gripping the bracket with surfaces of the tool formed from a material of sufficiently reduced hardness relative to the bracket hardness to avoid breaking the bracket during the pivoting step.

10. The method of claim 9, wherein the material is a nonmetallic material.

11. The method of claim 9, wherein the material is a ductile metallic material.

12. The method of claim 7, wherein the bracket is formed from a ceramic material.

13. A method of debonding a ceramic bracket having a base affixed to a tooth surface of a patient with an adhesive located between the base and the tooth, the ceramic bracket further having first and second opposite sides, an archwire slot, and a tool engagement portion disposed on at least the first side of the bracket, the method comprising:

engaging the tool engagement portion with a debonding tool, moving the tool to apply unequal forces to the first and second opposite sides of the ceramic bracket with the greater force being a tensile force applied to the first side in a direction away from the tooth surface, fracturing the adhesive between the base of the ceramic bracket and the tooth surface beginning at the first side under the greater tensile force, and removing the bracket from the tooth surface in a single piece.

14. The method of claim 13, wherein the step of moving the tool to apply the unequal forces further comprises:

pivoting the first side of the ceramic bracket with respect to the second side of the bracket about an axis lying in a plane generally parallel to the tooth surface.

* * * * *